(12) United States Patent
Kondo et al.

(10) Patent No.: US 7,615,669 B2
(45) Date of Patent: Nov. 10, 2009

(54) PROCESS FOR PRODUCING FLUORO-COMPOUNDS

(75) Inventors: Norihisa Kondo, Yamaguchi (JP); Akio Watanabe, Yamaguchi (JP); Hiroki Kanezaki, Yamaguchi (JP); Kosuke Kawada, Yamaguchi (JP)

(73) Assignee: Tosoh F-Tech, Inc., Yamaguchi (JP)

( * ) Notice: Subject to any disclaimer, the term of this patent is extended or adjusted under 35 U.S.C. 154(b) by 226 days.

(21) Appl. No.: 11/887,135

(22) PCT Filed: Mar. 22, 2006

(86) PCT No.: PCT/JP2006/305673

§ 371 (c)(1),
(2), (4) Date: Sep. 26, 2007

(87) PCT Pub. No.: WO2006/103985

PCT Pub. Date: Oct. 5, 2006

(65) Prior Publication Data

US 2009/0030228 A1    Jan. 29, 2009

(30) Foreign Application Priority Data

Mar. 28, 2005   (JP) .............................. 2005-092877

(51) Int. Cl.
  C07C 31/34    (2006.01)
  C07C 31/38    (2006.01)
(52) U.S. Cl. ................ 568/842; 560/227; 560/100; 560/111; 560/124; 560/145; 549/518
(58) Field of Classification Search ................ 568/842; 560/100, 111, 124, 145, 170, 227; 549/518
See application file for complete search history.

(56) References Cited

U.S. PATENT DOCUMENTS

| 3,929,769 A | 12/1975 | Kaufmann et al. |
| 5,780,672 A | 7/1998 | Pasenok et al. |
| 2005/0085474 A1 | 4/2005 | Ebenbeck et al. |

FOREIGN PATENT DOCUMENTS

| CA | 1020541 | 11/1977 |
| CA | 2181134 | 1/1997 |
| CH | 596 238 | 3/1978 |
| DE | 2 324 158 | 11/1973 |
| DE | 195 25 727 | 1/1997 |
| DE | 103 00 112 | 7/2004 |
| EP | 0 753 497 | 1/1997 |
| EP | 1 437 342 | 7/2004 |
| FR | 2 185 619 | 1/1974 |
| GB | 1 427 761 | 3/1976 |
| JP | 49-41356 | 4/1974 |
| JP | 9-48741 | 2/1997 |
| JP | 2004-231646 | 8/2004 |
| NL | 7306923 | 11/1973 |

OTHER PUBLICATIONS

Hudlicky, M., (Sterospecific synthesis of all four stereoisomers of 4-fluoroglutamic acid, 1993, Journal of Fluorine Chemistry, 60 (2-3), pp. 193-210 (abstract 3 pages).*
Edited by CSJ: The Chemical Society of Japan, 'Shin Jikken Kagaku Koza 14 Yuki Kagobutsu no Gosei to Hanno I', Maruzen Co., Ltd., pp. 310-311, Nov. 20, 1977.
International Search Report issued May 30, 2006 in the International (PCT) Application of which the present application is the U.S. National Stage.

* cited by examiner

Primary Examiner—Porfirio Nazario-Gonzalez
Assistant Examiner—Yate' K Cutliff
(74) Attorney, Agent, or Firm—Wenderoth, Lind & Ponack, L.L.P.

(57) ABSTRACT

The present invention provides a process for producing highly pure fluoro-compounds by making use of N-(2-chloro-1,1,2-trifluoroethyl)diethylamine. The process produces little or no chlorinated by-products. The present invention provides a process for producing a fluoro-compound, comprising fluorinating an alcohol derivative represented by the following general formula (I): $R^1R^2R^3COH$ (I), (wherein $R^1$ represents a hydrogen atom, a substituted or unsubstituted alkyl group, aryl group, alkylcarbonyl group, alkoxycarbonyl group, arylcarbonyl group or aryloxycarbonyl group; and $R^2$ and $R^3$ are each independently a substituted or unsubstituted alkyl group, aryl group, alkylcarbonyl group, alkoxycarbonyl group, arylcarbonyl group or aryloxycarbonyl group, wherein at least two of $R^1$, $R^2$ and $R^3$ may together form part of a ring structure, either with or without a heteroatom) with N,N-diethyl-2-chloro-1,1,2-trifluoroethylamine to form a fluoro-compound represented by the following general formula (2): $R^1R^2R^3CF$ (2), (wherein $R^1$, $R^2$ and $R^3$ are as defined above), the process being characterized in that an alcohol derivative represented by the following general formula (3): $R^4OH$ (3), (wherein $R^4$ represents a substituted or unsubstituted alkyl group or aryl group) is added to the reaction system.

4 Claims, No Drawings

PROCESS FOR PRODUCING FLUORO-COMPOUNDS

TECHNICAL FIELD

The present invention relates to a process for producing fluoro-compounds, useful intermediates in the production of pharmaceutical and agrochemical products.

BACKGROUND ART

Various fluorinating agents have been developed in order to obtain fluoro-compounds by fluorinating various compounds. Examples of fluorinating agents include fluorine gas, hydrogen fluoride, tetra-alkyl fluorides, alkali metal fluorides and hydrofluoric acid/pyridine. Nucleophilic fluorinating agents, such as diethylaminosulfur trifluoride (DAST), N,N-diethyl-1,1,2,3,3,3-hexafluoropropylamine (also known as Ishikawa's reagent) and N-(2-chloro-1,1,2-trifluoroethyl)diethylamine (also known as Yarovenko's reagent), are particularly effective in fluorinating hydroxyl groups and are thus widely used in studies.

Fluoro-compounds such as fluoroproline derivatives of hydroxyproline are highly useful intermediates in the production of pharmaceutical and agrochemical products.

For example, Patent Document 1 describes that fluoropyrrolidine derivatives derived from fluoroproline derivatives act as effective DPP-IV inhibitors and are useful in the treatment of diabetes, immune deficiencies, skin diseases and prostatomegaly.

DAST has several drawbacks wherein $SF_4$ used in the production of DAST is highly toxic and harmful, and DAST is too costly to be used in industrial applications. Furthermore, DAST is unstable at room temperature and generates explosive materials, so that storage and use of the material need to be strictly regulated. These drawbacks make DAST unsuitable for use in industrial-scale fluorination.

α,α-difluoroalkylamine fluorinating agents such as Ishikawa's reagent and Yarovenko's reagent are less costly and are considered more suitable for fluorinating hydroxyl groups than DAST.

However, the production of α,α-difluoroalkylamine fluorinating agents results in the formation of considerable amounts of by-products that must be removed by distillation so that the agents can be used in fluorination processes (Non-Patent Documents 1 through 3).

Though α,α-difluoroalkylamine fluorinating agents are more stable than DAST, distilling these agents on an industrial scale is a task of considerable difficulty.

To avoid the cumbersome distillation process, the present inventors used N-(2-chloro-1,1,2-trifluoroethyl)diethylamine, one of α,α-difluoroalkylamine fluorinating agents, in fluorinating different alcohol derivatives without distillation. However, this attempt led to the formation of chlorinated by-products in large amounts. These chlorinated products have boiling points and melting points similar to those of the desired fluorinated product and separating them required a substantial effort.

Patent Document 1 International Publication No. WO02/38541 Pamphlet

Non-Patent Document 1 Bull. Chem. Soc. Jpn, 52(11), 3377 (1979)

Non-Patent Document 2 Zh. Obshch. Khim., 29, 2159 (1959)

Non-Patent Document 3 Org. React., 21, 158 (1974)

DISCLOSURE OF THE INVENTION

Problems to be Solved by the Invention

Accordingly, it is an object of the present invention to provide a process for producing fluoro-compounds in high purity. The process is characteristic in that it uses less costly and readily handleable N-(2-chloro-1,1,2-trifluoroethyl)diethylamine and produces little or no chlorinated by-products.

Means for Solving the Problems

In view of the present state of the art, the present inventors have made extensive studies and found that the desired fluoro-compounds can be obtained in high purity and yield by adding a primary alcohol during the fluorination of secondary and tertiary alcohol derivatives.

Specifically, the present invention concerns a process for producing a fluoro-compound, comprising fluorinating an alcohol derivative represented by the following general formula (1):

$$R^1R^2R^3COH \quad (1)$$

(wherein $R^1$ represents a hydrogen atom, a substituted or unsubstituted alkyl group, aryl group, alkylcarbonyl group, alkoxycarbonyl group, arylcarbonyl group or aryloxycarbonyl group; and $R^2$ and $R^3$ are each independently a substituted or unsubstituted alkyl group, aryl group, alkylcarbonyl group, alkoxycarbonyl group, arylcarbonyl group or aryloxycarbonyl group, wherein at least two of $R^1$, $R^2$ and $R^3$ may together form part of a ring structure, either with or without a heteroatom) with N,N-diethyl-2-chloro-1,1,2-trifluoroethylamine to form a fluoro-compound represented by the following general formula (2):

$$R^1R^2R^3CF \quad (2)$$

(wherein $R^1$, $R^2$ and $R^3$ are as defined above), the process being characterized in that an alcohol derivative represented by the following general formula (3):

$$R^4OH \quad (3)$$

(wherein $R^4$ represents a substituted or unsubstituted alkyl group or aryl group) is added to the reaction system.

EFFECTS OF THE INVENTION

Taking advantage of less costly and readily handleable N-(2-chloro-1,1,2-trifluoroethyl)diethylamine, the present invention enables low-cost production of highly pure fluoro-compounds with little or no chlorinated by-products produced.

BEST MODE FOR CARRYING OUT THE INVENTION

The present invention will now be described in detail.

The alcohol derivatives used as a raw material in the present invention represented by the general formula (1) are secondary and tertiary alcohols having a hydroxyl group.

The term "alkyl group" as used with reference to the above-described general formulas (1), (2) and (3) refers to an alkyl group having 1 to 20 carbon atoms. Examples thereof include methyl, ethyl, n-propyl, isopropyl, n-butyl, s-butyl, t-butyl, n-pentyl, 1-methylbutyl, 2-methylbutyl, 3-methylbutyl, 1-ethylpropyl, cyclohexyl, cyclopentyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, adamantyl, menthyl, norbornyl, bicyclohexyl, n-nonyl, n-decyl and n-dodecyl. The alkyl group may be substituted with a halogen atom, a cyano group, an aryl group, an acyl group, an alkoxy group, an aryloxy group, an acyloxy group, an alkoxycarbonyl group, an aryloxycarbonyl group, an alkanesulfonyl group, an arylsulfonyl group or an acylamino group.

The term "aryl group" as used with reference to the above-described general formulas (1), (2) and (3) refers to an aromatic group having 6 to 20 carbon atoms. Examples thereof include phenyl, benzyl, mesityl, phenetyl, tolyl, trityl, naphthyl, anthracenyl, indolyl and biphenyl. The aryl group may be substituted with an alkyl group, a halogen atom, a cyano group, a nitro group, an acyl group, an alkoxy group, an aryloxy group, an acyloxy group, an alkoxycarbonyl group, an aryloxycarbonyl group, an alkanesulfonyl group, an arylsulfonyl group or an acylamino group.

The term "alkylcarbonyl group" as used with reference to the above-described general formulas (1) and (2) refers to an alkylcarbonyl group having 2 to 20 carbon atoms. The alkylcarbonyl group may be exemplified as in the above alkyl group and may be substituted with similar substituents.

The term "alkoxycarbonyl group" as used with reference to the above-described general formulas (1) and (2) refers to an alkoxycarbony group having 2 to 20 carbon atoms. The alkoxycarbonyl group may be exemplified as in the above alkyl group and may be substituted with similar substituents.

The term "arylcarbonyl group" as used with reference to the above-described general formulas (1) and (2) refers to an arylcarbonyl group having 7 to 20 carbon atoms. The arylcarbonyl group may be exemplified as in the above aryl group and may be substituted with similar substituents.

The term "aryloxycarbonyl group" as used with reference to the above-described general formulas (1) and (2) refers to an aryloxycarbonyl group having 7 to 20 carbon atoms. The aryloxycarbonyl group may be exemplified as in the above aryl group and may be substituted with similar substituents.

At least two of $R^1$, $R^2$ and $R^3$ may together form part of a ring structure, either with or without a heteroatom. The substituent may be cyclopentyl, cyclohexyl, pyrrolidinyl, adamantyl, norbornyl, piperadinyl, piperidinyl or morpholinyl.

The halogen atom may be fluorine, chlorine, bromine or iodine.

The alcohol derivative of the general formula (1) is preferably 2-propanol, 2-butanol, tert-butanol, 3-methyl-2-butanol, 2,3-dimethyl-2-butanol, 3,3-dimethyl-2-butanol, 2-pentanol, 3-pentanol, 4-methyl-2-pentanol, 3-hexanol, cyclopentanol, cyclohexanol, 1-methylcyclohexanol, 2-methylcyclohexanol, tetrahydro-4-pyranol, 2-norborneol, menthol, 1-adamantanol, 2-adamantanol, 1-phenylethanol, 1-phenyl-1-propanol, 1,2,3,4-tetrahydro-1-naphthol, ethyl mandelate, ethyl 2-hydroxyisobutyrate, N-(tert-butoxycarbonyl)-4-hydroxy-proline methyl ester, N-benzyl-4-hydroxy-proline methyl ester, N-(fluorenylmethoxycarbonyl)-4-hydroxy-proline methyl ester or N-benzyloxycarbonyl-4-hydroxy-proline methyl ester.

The fluoro-compound of the general formula (2) is preferably 2-fluoropropane, 2-fluorobutane, tert-butylfluoride, 2-fluoro-3-methylbutane, 2,3-dimethyl-2-fluorobutane, 3,3-dimethyl-2-fluoropentane, 2-fluoropentane, 3-fluoropentane, 2-fluoro-4-methylpentane, 3-fluorohexane, fluorocyclopentane, fluorocyclohexane, 1-fluoro-1-methylcyclohexane, 1-fluoro-2-methylcyclohexane, tetrahydro-4-fluoropyran, 2-fluoronorbornene, menthylfluoride, 1-fluoroadamantane, 2-fluoroadamantane, 1-fluoro-1-phenyl ethane, 1-fluoro-1-phenylpropane, 1-fluoro-1,2,3,4-tetrahydronaphthalene, ethyl α-fluorophenylacetate, ethyl 2-fluoroisobutyrate, N-(tert-butoxycarbonyl)-4-fluoro-proline methyl ester, N-benzyl-4-fluoro-proline methyl ester, N-(fluorenylmethoxycarbonyl)-4-fluoro-proline methyl ester or N-benzyloxycarbonyl-4-fluoro-proline methyl ester.

The alcohol derivative of the general formula (3) is preferably methanol, ethanol, 1-propanol, 1-butanol, 3-methyl-1-butanol, 3,3-dimethyl-1-butanol, 1-pentanol, 4-methyl-1-pentanol, 1-hexanol or benzyl alcohol. Of these, methanol and ethanol are particularly preferred.

N,N-diethyl-2-chloro-1,1,2-trifluoroethylamine, the fluorinating agent for use in the present invention, can be produced by a known technique (Org. React., 21, 158 (1974)).

The fluorination process may be carried out either in the absence or in the presence of a solvent. While any solvent may be used that is aprotic and inert to the fluorination, preferred are hydrocarbons, such as pentane and hexane, ketones, such as acetone, methyl ethyl ketone and methyl isobutyl ketone, halogenated hydrocarbons, such as dichloromethane, dibromomethane, chloroform, bromoform, carbon tetrachloride, 1,2-dichloroethane and 1,1,2-trichloroethane, ethers, such as dimethyl ether, diethyl ether, 1,4-dioxane and tetrahydrofuran, aromatic hydrocarbons, such as benzene, toluene and xylene, and aprotic polar solvents, such as acetonitrile, sulfolane, N,N-dimethylacetamide, N,N-dimethylformamide, dimethylsulfoxide, N-methylpyrrolidone and N,N-dimethylimidazolidinone. These solvents may be used either individually or in combination of two or more. Of these solvents, chloroform, dichloromethane, tetrahydrofuran and acetonitrile are particularly preferred.

For fluorination, the alcohol derivatives of the general formulas (1) and (3) and when necessary, a solvent, are placed in a reaction vessel and stirred. N,N-diethyl-2-chloro-1,1,2-trifluoroethylamine is then added either directly or in a solvent and the mixture is further stirred.

Regarding the order that the components are added, N,N-diethyl-2-chloro-1,1,2-trifluoroethylamine, either dissolved in a solvent or not, may first be placed in the vessel with the alcohol derivative of the general formula (3), and the alcohol derivative of the general formula (1), either dissolved in a solvent or not, may subsequently be added.

Alternatively, N,N-diethyl-2-chloro-1,1,2-trifluoroethylamine may be generated in the reaction system.

The alcohol derivative of the general formula (3) is added preferably at a molar ratio to the alcohol derivative of the general formula (1) of 0.01 to 0.5, and more preferably at a molar ratio of 0.1 to 0.3.

While N,N-diethyl-2-chloro-1,1,2-trifluoroethylamine may be used in any amount equal to, or greater than, the theoretical amount of the alcohol derivative of the general formula (1) and the alcohol derivative of the general formula (3) combined, it is preferably used in an amount of 1 to 10 mol, and more preferably in an amount of 1.1 to 2 mol with respect to 1 mol of the theoretical amount of the alcohol derivative of the general formula (1) and the alcohol derivative of the general formula (3) combined.

While N,N-diethyl-2-chloro-1,1,2-trifluoroethylamine maybe added to the reaction system at any temperature, it is preferably added at a temperature of −40 to 100° C. and more preferably added at a temperature of −10 to 50° C.

While the fluorination may be carried out at any temperature between 10 and 100° C., the preferred temperature range is from 10 to 50° C.

The reaction mixture is stirred at a speed that ensures thorough stirring of the mixture.

The reaction is generally complete in 1 to 24 hours though the time may vary.

The desired product can be obtained from the reaction mixture by common techniques.

EXAMPLES

The present invention will now be described with reference to examples, which are not intended to limit the scope of the invention in any way. The following compound is used throughout Examples and Comparative Examples (The compound is assigned the code CTT.):

CTT: N-(2-chloro-1,1,2-trifluoroethyl)diethylamine

In each experiment, the reaction mixture was analyzed by gas chromatography (TC-1, 30 m, GL Sciences, or CP-Sil8CB, 50 m, GL Sciences). The amount of the chlorinated product (wt %) was determined as (Chlorinated product/Fluorinated product)×100.

The yield of the desired product was determined by integrating $^{19}$F-NMR spectra.

Example 1

Cyclopentanol (4.31 g, 50 mmol) and methanol (0.24 g, 7.5 mmol) were dissolved in chloroform (12 g). While the reaction mixture was kept at 0° C. or below, CTT (14.22 g, 75 mmol) was added. The mixture was heated to 30° C. and was stirred for 15 hours. Subsequently, the mixture was analyzed by gas chromatography to confirm that the reaction was complete and determine the amount of the chlorinated product (0.5 wt %). Water was then added and the organic layer was separated and concentrated to obtain fluorocyclopentane (78% yield).

Example 2

Cyclopentanol (4.31 g, 50 mmol) and methanol (0.24 g, 7.5 mmol) were dissolved in chloroform (16 g). While the reaction mixture was kept at 0° C. or below, CTT (11.38 g, 60 mmol) was added. The mixture was heated to 25° C. and was stirred for 20 hours. Subsequently, the mixture was analyzed by gas chromatography to confirm that the reaction was complete and determine the amount of the chlorinated product (0.2 wt %). Water was then added and the organic layer was separated and concentrated to obtain fluorocyclopentane (75% yield).

Example 3

Cyclopentanol (4.31 g, 50 mmol) and ethanol (0.35 g, 7.5 mmol) were dissolved in chloroform (20 g). While the reaction mixture was kept at 5° C. or below, CTT (18.96 g, 100 mmol) was added. The mixture was heated to 50° C. and was stirred for 12 hours. Subsequently, the mixture was analyzed by gas chromatography to confirm that the reaction was complete and determine the amount of the chlorinated product (0.8 wt %). Water was then added and the organic layer was separated and concentrated to obtain fluorocyclopentane (74% yield).

Example 4

Cyclopentanol (4.31 g, 50 mmol) and methanol (0.48 g, 15 mmol) were dissolved in chloroform (12 g). While the reaction mixture was kept at 10° C. or below, CTT (14.22 g, 75 mmol) was added. The mixture was heated to 30° C. and was stirred for 15 hours. Subsequently, the mixture was analyzed by gas chromatography to confirm that the reaction was complete and determine the amount of the chlorinated product (0.1 wt %). Water was then added and the organic layer was separated and concentrated to obtain fluorocyclopentane (76% yield).

Example 5

2-pentanol (4.41 g, 50 mmol) and methanol (0.24 g, 7.5 mmol) were dissolved in chloroform (18 g). While the reaction mixture was kept at 0° C. or below, CTT (14.22 g, 75 mmol) was added. The mixture was heated to 30° C. and was stirred for 15 hours. Subsequently, the mixture was analyzed by gas chromatography to confirm that the reaction was complete and determine the amount of the chlorinated product (0.3 wt %). Water was then added and the organic layer was separated and concentrated to obtain 2-fluoropentane (83% yield).

Example 6

1-adamantanol (4.57 g, 30 mmol) and methanol (0.14 g, 4.5 mmol) were dissolved in chloroform (30 g). While the reaction mixture was kept at 0° C. or below, CTT (8.53 g, 45 mmol) was added. The mixture was heated to 50° C. and was stirred for 15 hours. Subsequently, the mixture was analyzed by gas chromatography to confirm that the reaction was complete and determine the amount of the chlorinated product (0.2 wt %). Water was then added and the organic layer was separated and concentrated to obtain 1-fluoroadamantane (87% yield).

Example 7

Ethyl mandelate (5.41 g, 30 mmol) and methanol (0.14 g, 4.5 mmol) were dissolved in chloroform (12 g). While the reaction mixture was kept at 0° C. or below, CTT (8.53 g, 45 mmol) was added. The mixture was heated to 30° C. and was stirred for 15 hours. Subsequently, the mixture was analyzed by gas chromatography to confirm that the reaction was complete and determine the amount of the chlorinated product (0.5 wt %). Water was then added and the organic layer was separated and concentrated to obtain ethyl α-fluorophenylacetate (88% yield).

Example 8

Ethyl 2-hydroxyisobutyrate (3.96 g, 30 mmol) and methanol (0.14 g, 4.5 mmol) were dissolved in chloroform (16 g). While the reaction mixture was kept at 0° C. or below, CTT (8.53 g, 45 mmol) was added. The mixture was heated to 30° C. and was stirred for 15 hours. Subsequently, the mixture was analyzed by gas chromatography to confirm that the reaction was complete and determine the amount of the chlorinated product (0.2 wt %). Water was then added and the organic layer was separated and concentrated to obtain ethyl 2-fluoroisobutyrate (84% yield).

Example 9

N-(tert-butoxycarbonyl)-4-hydroxy-proline methyl ester (4.91 g, 20 mmol) and methanol (0.10 g, 3 mmol) were dissolved in chloroform (18 g). While the reaction mixture was kept at 0° C. or below, CTT (5.69 g, 30 mmol) was added. The mixture was heated to 30° C. and was stirred for 15 hours.

Subsequently, the mixture was analyzed by gas chromatography to confirm that the reaction was complete and determine the amount of the chlorinated product (0.3 wt %). Water was then added and the organic layer was separated and concentrated to obtain N-(tert-butoxycarbonyl)-4-fluoro-proline methyl ester (86% yield).

Comparative Example 1

Cyclopentanol (4.31 g, 50 mmol) was dissolved in chloroform (12 g). While the reaction mixture was kept at 0° C. or below, CTT (14.22 g, 75 mmol) was added. The mixture was heated to 30° C. and was stirred for 15 hours. Subsequently, the mixture was analyzed by gas chromatography to confirm that the reaction was complete and determine the amount of the chlorinated product (8.6 wt %). Water was then added and the organic layer was separated and concentrated to obtain fluorocyclopentane (69% yield).

Comparative Example 2

2-pentanol (4.41 g, 50 mmol) was dissolved in chloroform (18 g). While the reaction mixture was kept at 0° C. or below, CTT (14.22 g, 75 mmol) was added. The mixture was heated to 30° C. and was stirred for 15 hours. Subsequently, the mixture was analyzed by gas chromatography to confirm that the reaction was complete and determine the amount of the chlorinated product (7.5 wt %). Water was then added and the organic layer was separated and concentrated to obtain fluorocyclopentane (76% yield).

Comparative Example 3

1-adamantanol (4.57 g, 30 mmol) was dissolved in chloroform (30 g). While the reaction mixture was kept at 0° C. or below, CTT (8.53 g, 45 mmol) was added. The mixture was heated to 50° C. and was stirred for 15 hours. Subsequently, the mixture was analyzed by gas chromatography to confirm that the reaction was complete and determine the amount of the chlorinated product (10.6 wt %). Water was then added and the organic layer was separated and concentrated to obtain 1-fluoroadamantane (76% yield).

Comparative Example 4

Ethyl mandelate (5.41 g, 30 mmol) was dissolved in chloroform (12 g). While the reaction mixture was kept at 0° C. or below, CTT (8.53 g, 45 mmol) was added. The mixture was heated to 30° C. and was stirred for 15 hours. Subsequently, the mixture was analyzed by gas chromatography to confirm that the reaction was complete and determine the amount of the chlorinated product (7.2 wt %). Water was then added and the organic layer was separated and concentrated to obtain ethyl α-fluorophenylacetate (81% yield).

Comparative Example 5

Ethyl 2-hydroxyisobutyrate (3.96 g, 30 mmol) was dissolved in chloroform (16 g). While the reaction mixture was kept at 0° C. or below, CTT (8.53 g, 45 mmol) was added. The mixture was heated to 30° C. and was stirred for 15 hours. Subsequently, the mixture was analyzed by gas chromatography to confirm that the reaction was complete and determine the amount of the chlorinated product (6.9 wt %). Water was then added and the organic layer was separated and concentrated to obtain ethyl 2-fluoroisobutyrate (78% yield).

Comparative Example 6

N-(tert-butoxycarbonyl)-4-hydroxy-proline methyl ester (4.91 g, 20 mmol) was dissolved in chloroform (18 g). While the reaction mixture was kept at 0° C. or below, CTT (5.69 g, 30 mmol) was added. The mixture was heated to 30° C. and was stirred for 15 hours. Subsequently, the mixture was analyzed by gas chromatography to confirm that the reaction was complete and determine the amount of the chlorinated product (9.3 wt %). Water was then added and the organic layer was separated and concentrated to obtain N-(tert-butoxycarbonyl)-4-fluoro-proline methyl ester (76% yield).

INDUSTRIAL APPLICABILITY

Traditionally, fluoro-compounds have been produced by fluorinating alcohol derivatives with diethylaminosulfur trifluoride (DAST). However, DAST requires strict regulations regarding its storage and use and is thus considered unsuitable for use in industrial-scale fluorination. In contrast, α,α-difluoroalkylamine fluorinating agents are less costly reagents suitable for industrial fluorination of hydroxyl groups. Nonetheless, these α,α-difluoroalkylamine fluorinating agents have a drawback that the significant amounts of by-products formed during the production must be removed by distillation in order to make the agents usable in the fluorination processes.

Although α,αdifluoroalkylamine fluorinating agents are more stable than DAST, distilling these agents on an industrial scale is a task of considerable difficulty. One approach to avoid the distillation process is the use of N-(2-chloro-1,1,2-trifluoroethyl)diethylamine, one of the α,α-difluoroalkylamine fluorinating agents. While this compound can be used to fluorinate different alcohol derivatives without distillation, the process generally results in the formation of chlorinated by-products in large amounts. These chlorinated products have boiling points and melting points similar to those of the desired fluorinated product and separating them requires a substantial effort.

The present invention enables the production of highly pure fluoro-compounds by making use of less costly and readily handleable N-(2-chloro-1,1,2-trifluoroethyl)diethylamine, while significantly reducing the chlorinated by-products and the production cost. The present invention therefore provides significant economical benefits.

The invention claimed is:

1. A process for producing a fluoro-compound, comprising fluorinating an alcohol derivative represented by the following general formula (1):

$$R^1R^2R^3COH \quad (1)$$

(wherein $R^1$ represents a hydrogen atom, a substituted or unsubstituted alkyl group, aryl group, alkylcarbonyl group, alkoxycarbonyl group, arylcarbonyl group or aryloxycarbonyl group; and $R^2$ and $R^3$ are each independently a substituted or unsubstituted alkyl group, aryl group, alkylcarbonyl group, alkoxycarbonyl group, arylcarbonyl group or aryloxycarbonyl group, wherein at least two of $R^1$, $R^2$ and $R^3$ may together form part of a ring structure, either with or without a heteroatom) with N,N-diethyl-2-chloro-1,1,2-trifluoroethylamine to form a fluoro-compound represented by the following general formula (2):

$$R^1R^2R^3CF \quad (2)$$

(wherein $R^1$, $R^2$ and $R^3$ are as defined above), the process being characterized in that an alcohol derivative represented by the following general formula (3):

$$R^4OH \quad (3)$$

(wherein R⁴ represents a substituted or unsubstituted alkyl group or aryl group) is added to the reaction system.

2. The process for producing a fluoro-compound according to claim 1, wherein the alcohol derivative represented by the general formula (3) is added at a molar ratio to the alcohol derivative of the general formula (1) of 0.01 to 0.5.

3. The process for producing a fluoro-compound according to claim 1, wherein R⁴ in the alcohol derivative represented by the general formula (3) is methyl or ethyl.

4. The process for producing a fluoro-compound according to claim 2, wherein R⁴ in the alcohol derivative represented by the general formula (3) is methyl or ethyl.

* * * * *